(12) United States Patent
Plant (10) Patent No.: US 7,956,998 B2
(45) Date of Patent: Jun. 7, 2011

(54) METHOD AND SYSTEM FOR THE POLARMETRIC ANALYSIS OF SCATTERING MEDIA UTILISING POLARIZATION DIFFERENCE SENSING (PDS)

(76) Inventor: James Plant, Victoria (CA)

( * ) Notice: Subject to any disclaimer, the term of this patent is extended or adjusted under 35 U.S.C. 154(b) by 316 days.

(21) Appl. No.: 12/204,203

(22) Filed: Sep. 4, 2008

(65) Prior Publication Data

US 2009/0059227 A1 Mar. 5, 2009

Related U.S. Application Data

(60) Provisional application No. 60/969,744, filed on Sep. 4, 2007.

(51) Int. Cl.
  G01N 21/00 (2006.01)
  G01J 4/00 (2006.01)
(52) U.S. Cl. ......... 356/364; 356/335; 356/336; 356/337
(58) Field of Classification Search .......... 356/364–369, 356/335, 336, 337, 341, 343, 327
See application file for complete search history.

(56) References Cited

U.S. PATENT DOCUMENTS

| | | | |
|---|---|---|---|
| 3,888,269 A | | 6/1975 | Bashark |
| 3,904,293 A | * | 9/1975 | Gee ................................ 356/369 |
| 5,017,497 A | * | 5/1991 | Gerard de Grooth et al. .. 436/63 |
| 5,586,567 A | | 12/1996 | Smith et al. |
| 7,387,688 B2 | | 6/2008 | Jung et al. |
| 7,392,813 B2 | | 7/2008 | Betram et al. |
| 7,400,407 B2 | | 7/2008 | Ng et al. |
| 7,630,075 B2 | * | 12/2009 | Fritz ............................. 356/337 |

* cited by examiner

*Primary Examiner* — L. G Lauchman
(74) *Attorney, Agent, or Firm* — Davis & Bujold, P.L.L.C.

(57) ABSTRACT

A method for polarmetric analysis of scattering media. A first step involves directing stimulus from a linearly polarized stimulus source at a sample. A second step involves directing the stimulus coming from the sample through a collimating system into a polarization segregation unit which causes the stimulus to be segregated into a linearly polarized unscattered component and a depolarized scattered component. A third step involves quantification of scattering processes through computationally comparing the unscattered component and the scattered component.

2 Claims, 7 Drawing Sheets

METHOD AND SYSTEM FOR THE POLARMETRIC ANALYSIS OF SCATTERING MEDIA UTILISING POLARIZATION DIFFERENCE SENSING (PDS)

FIELD OF THE INVENTION

The present invention relates to analytical technique which can discriminate and determine the magnitude and characteristics of scattering processes caused by suspended bubbles, droplets of fluids or particulate matter in an optically (or electromagnetically) transmissive environment, such as air, vacuum, surrounding fluid or solid medium.

BACKGROUND OF THE INVENTION

The accurate measurement of turbidity has been an urgent requirement in a number of diverse analytical, engineering and manufacturing settings. For example, applications for turbidity sensor technology range from the manufacturing of pharmaceuticals and medical devices, to water purification, environmental monitoring and the control of dishwashing and clothes washing machine operation. In its simplest form, a turbidity sensor consists of a light emitter separated from a light intensity sensor by a volume or flow of a sample to be analysed. As the turbidity of a sample increases, the intensity of the light transmitted directly along the optical path and falling on the light sensor decreases (thus giving a crude measure of the turbidity of the sample). Although adequate for many applications, this basic form of turbidity sensor cannot distinguish between a decrease in the received signal caused by absorption by the intervening medium or suspended particles, by the effect of actual scattering caused by suspended particulate matter along the optical path, or by systematic variability caused by fluctuations in emitter or detector performance (i.e., variability caused by emitter and sensor temperature fluctuations).

A more sophisticated, accurate and common form of turbidity sensor consists of a single light emitter positioned inline with a light detector on a common optical axis, and a secondary light detector positioned at 90° relative to the optical axis of the first emitter detector pair. In this off axis position, the second light detector's input is proportional to the amount of the emitter's output which has been scattered or reflected perpendicular to the original optical axis. When analysed in conjunction with the output of the on-axis detector's output, a ratiometric estimate of turbidity or scattering can be achieved which is relatively immune to systematic measurement errors, or errors introduced by absorption by the suspended particles or sample medium. It is important to note, however, that under extreme turbid conditions the amount of the scattered signal able to reach the off axis detector can decrease to such an extent that the ratiometric output becomes meaningless. In addition, the requirement of a secondary off axis detector limits present turbidity sensors to the detection and quantification of turbidity in fluid mediums, or small samples of solid material.

SUMMARY OF THE INVENTION

A method for polarmetric analysis of scattering media. A first step involves directing stimulus from a linearly polarized stimulus source at a sample. A second step involves directing the stimulus coming from the sample through a collimating system into a polarization segregation unit which is aligned (relative to the orientation of the emitted linearly polarized stimulus) in such a way so that it causes the transmitted stimulus to be segregated into a linearly polarized unscattered component (with the same orientation of the original emitted stimulus) and a scattered depolarized component. A third step involves computationally comparing the unscattered component and the scattered component.

BRIEF DESCRIPTION OF THE DRAWINGS

These and other features of the invention will become more apparent from the following description in which reference is made to the appended drawings, the drawings are for the purpose of illustration only and are not intended to in any way limit the scope of the invention to the particular embodiment or embodiments shown, wherein.

DETAILED DESCRIPTION OF THE PREFERRED EMBODIMENT

The preferred embodiment, a Method and System for the Polarmetric Analysis of Scattering Media, will now be described with reference to FIGS. 1 through 7.

Figure 6:
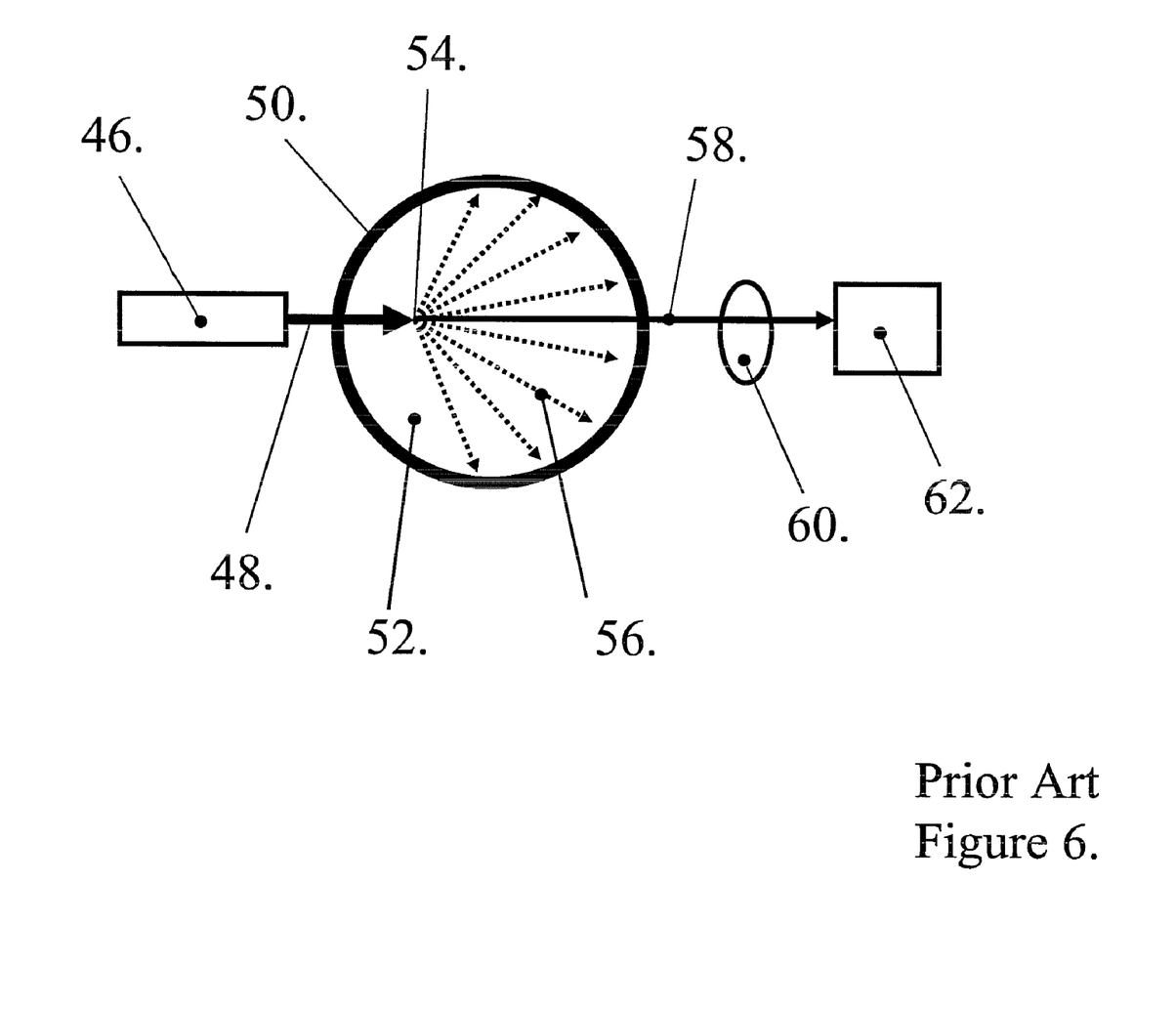
FIG. 6, labelled as Prior Art, is a schematic diagram which illustrates the basic configuration of a turbidity sensor having a single in-line emitter and detector pair.

Referring to FIG. 6, which is labeled as Prior Art, there is illustrated a basic form of turbidity sensor. Such turbidity sensors are comprised of an inline emitter 46, and a detector 62. Emitter 46 produces non-polarized illumination 48 which passes through a sample chamber 50 containing a sample media 52. As non-polarized illumination 48 passes through sample media 52, it interacts with suspended particulate matter 54 to cause an increase in scattering 56 of the stimulus throughput. As a result, increased turbidity of the sample results in a decrease stimulus throughput 58 which can be focused, by focal lens 60, on to detector 62. While capable of generating a crude measure of turbidity, this form of sensor cannot distinguish between a reduction in the stimulus throughput caused by increased scattering from suspended particles (e.g. turbidity) or a decrease in the stimulus transmission caused by increased absorption within the sample media. This configuration is also prone to measurement errors due to systematic variations in emitter and detector performance such as those caused by fluctuations in ambient temperature.

Figure 7:
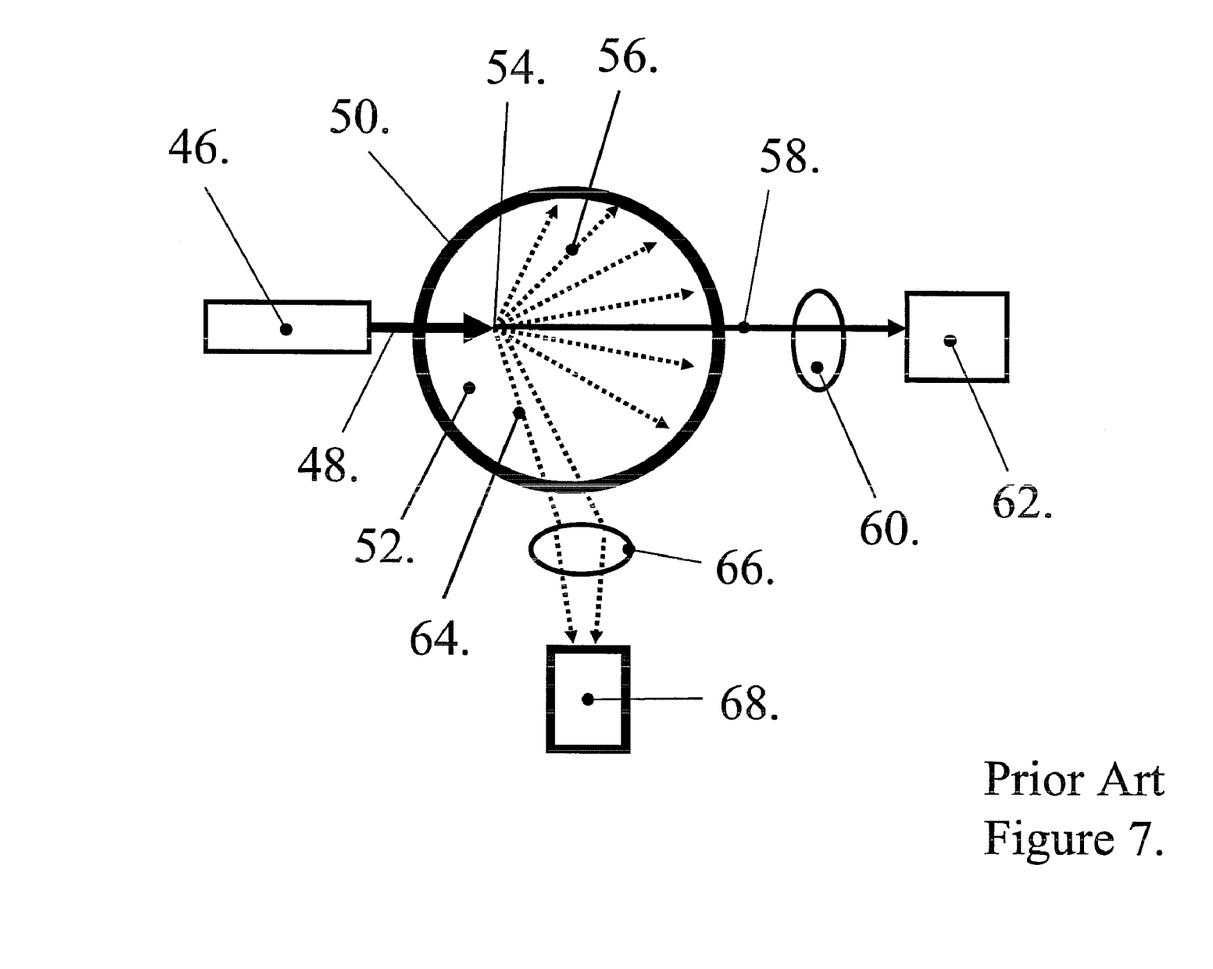
FIG. 7, labelled as Prior Art, is a schematic diagram which illustrates the more common form of a turbidity sensor having a secondary receptor situated 90° (or more) off of the optical axis of the primary in-line emitter detector pair.

Referring to FIG. 7, labeled as Prior Art, there is illustrated a more common and practical form of turbidity sensor comprised of an inline emitter 46 and a detector pair, including a primary detector 62 and a secondary detector 68 situated at an angle off of primary optical axis 58. As above, the emitter typically produces non-polarised illumination 48 which passes through a sample chamber 50 containing a sample medium 52. As non-polarized illumination 48 passes through sample media 52, it interacts with suspended particles 54. Scattering induced by suspended particulate matter results in a decrease in the amount of stimulus throughput along the original optical axis 58, and a decrease in the intensity of the throughput which is focused, by primary focal lens 60, on to primary detector 62. A portion of the stimulus 64 which is scattered off of the primary optical axis 58 exits sample chamber 50 and is focused, by secondary focal lens 66, onto a secondary detector 68. Secondary detector 68 is, typically, positioned between 90° and 170° relative to primary optical axis 58. The output signals of on axis primary detector 62 and off axis secondary detector 68 are computationally compared to create an estimate of sample turbidity that is relatively free of common mode noise and absorption artifacts. While this form of turbidity sensor is useful for estimating turbidity over a very wide range of values, it is important to note that as sample turbidity or opaqueness increases it can reach a point where there is inadequate scattered stimuli reaching the off axis detector, secondary detector 68. Under such conditions the turbidity sensor fails due to the ratiometric nature of the comparison between the two detectors outputs.

The present invention utilises the fact that, when linearly polarized light passes through a scattering medium, the portion of the stimulus which is scattered or reflected off suspended particles becomes randomly polarized. As a result, if one begins with an emitter producing a linearly polarized light output (such as a laser), any decrease in intensity of the stimulus throughput at that specific linear polarization orientation (and subsequent increase in intensity at any other polarization angle) is due to the effect of scattering. It is important to note that, although only one optical path is utilised (that is, no secondary detector positioned 90° relative to the emitters optical axis is required), this novel analytical method for polarmetric turbidity sensing produces two forms of data (polarized and depolarized throughput) which can be used to create a sensitive, accurate and error-free computational estimate of turbidity or scattering.

Since such a polarmetric turbidity sensor does not rely on measurements of off axis scattered light (and records only throughput along the emitter/detector pair's optical axis), this form of turbidity sensor can be configured to operate through optically or electromagnetically dense materials or solutions (for example, to detect and quantify suspended particles in oil). It is important to note that the underlying principle of this polarmetric scattering effect is not constrained to optical wavelengths, and therefore can be applied for the analysis of samples which are typically beyond the scope of traditional turbidity measurement techniques. For example, utilising linearly polarized microwave, radio or x-ray emissions, accurate real-time measurement of particulate suspension in materials such as concrete or cement can be carried out to ensure homogeneous consistency during the pouring, settling and curing phases, and for the nondestructive examination of the level of homogeneity of particle distribution in the completed structures. In addition, linearly polarized stimuli can be reflected off the target surface, and changes in the proportion of polarized and depolarized components within the returned signal can be determined over time. Alternately, mapping of surface texture can be carried out by varying the spatial localization of the polarized stimulus on the target surface, while calculating the proportion of depolarization at each spatial location.

The present polarmetric method for determining turbidity has the unique ability to unambiguously differentiate the independent effects of scattering and absorption. As such, this allows for a more extensive and quantitative analysis of a turbidity sample. For example, if a broadband linearly polarized stimulus is used, and the stimulus is broken down into its spectral components (after passing through the scattering medium and polarization segregating mechanisms), one can determine the wavelengths at which any scattering occurred. Since each size of particle will preferentially scatter the linearly polarized stimulus at a specific wavelength, our polarmetric turbidity sensor has the unique ability to give a measure of the size distribution of the scattering particles within the sample being studied.

The ability of this technique to assess both temporal and spatial variations within scattering media allows for the creation of engineered materials having spatial patterns creating greater or lesser scattering, or unique patterns of scattering at different wavelengths of stimulus. The use of such engineered materials could be applied to fight counterfeiting by embedding the scattering material in either inks and dyes, or the underlying material substrate they are applied to during the printing process. In addition, the ability to isolate and calculate absorption specific effects allows for the further potential simultaneous application of a spectrographic analysis of the sample's chemical composition.

Figure 1:
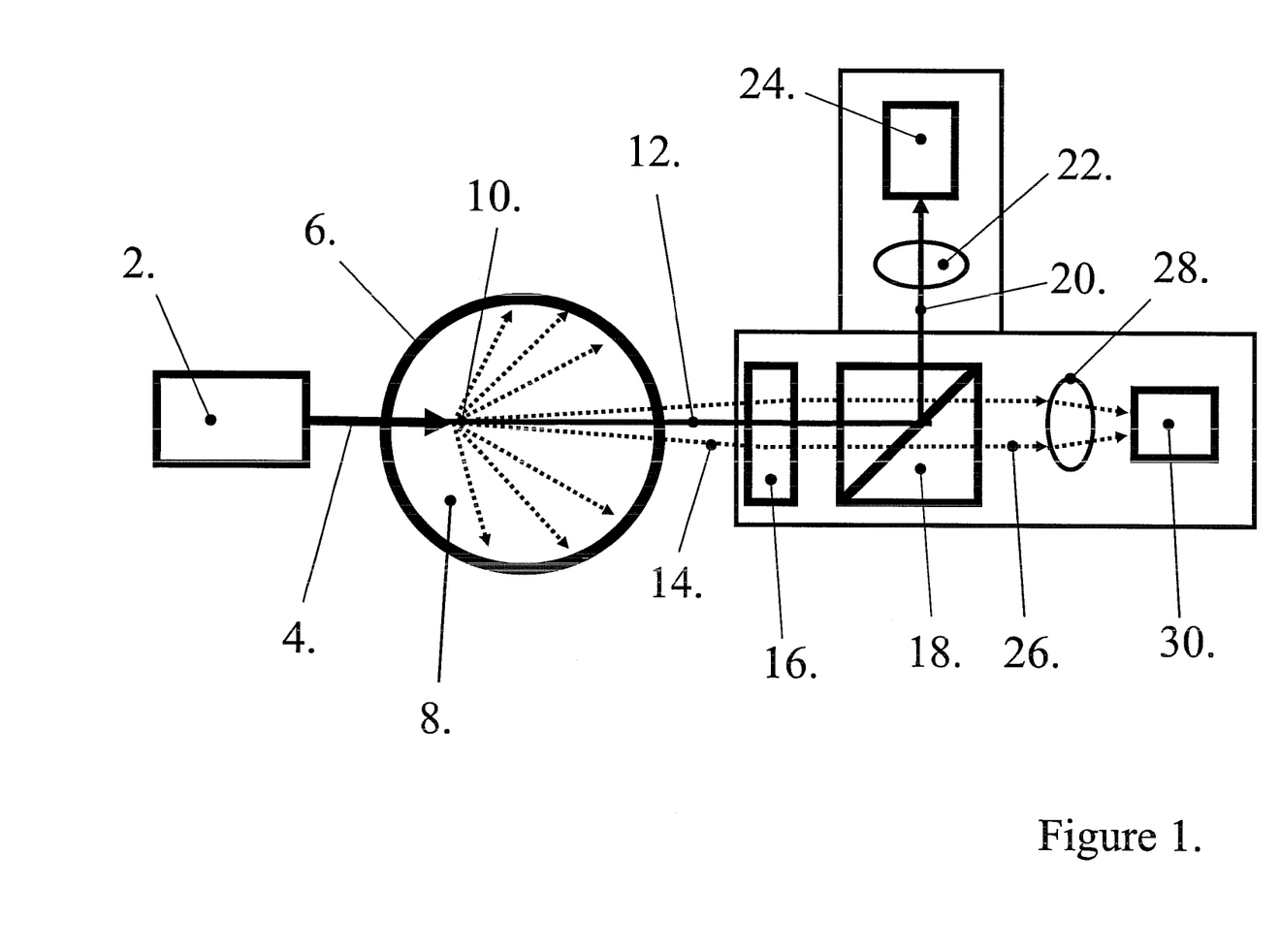
FIG. 1 is a schematic diagram of a method and system for the polarmetric analysis of scattering media utilising Polarization Different Sensing (PDS). In this application, PDS is utilised to characterise and quantify the turbidity of a fluid sample.

Referring to a FIG. 1, a light source (such as a laser 2) emits a linearly polarizer stimulus 4 which projects through a sample chamber 6. If a sample medium 8 in sample chamber 6 contains scattering particles, a portion of the linearly polarized light will undergo scattering 10 and depolarization. The stimulus throughput (which passes through sample media 8 and exits sample chamber 6) is comprised of horizontally polarized throughput 12 (with the same orientation of linear polarization) and scattered randomly polarized throughput 14. These two components of the stimulus throughput then pass through a collimating system 16 so that the stimulus beams are a parallel to the optical axis. The collimated stimulus throughput enters a polarization segregation unit (in this case a polarizing beam splitter cube 18, having an orientation which would match and isolate the orientation of the original linearly polarized stimulus) in such a way as to divert the horizontally linearly polarized and unscattered component 20 through a focusing apparatus 22 on to a sensor 24. All remaining stimulus throughput, having undergone scattering by the sample media, possess random angles of linear polarization and pass through 26 the polarization segregation unit, a focusing apparatus 28 and onto a second sensor 30. The outputs from sensor 24 and 30 are then computationally compared to create an estimation of sample turbidity.

Figure 2:
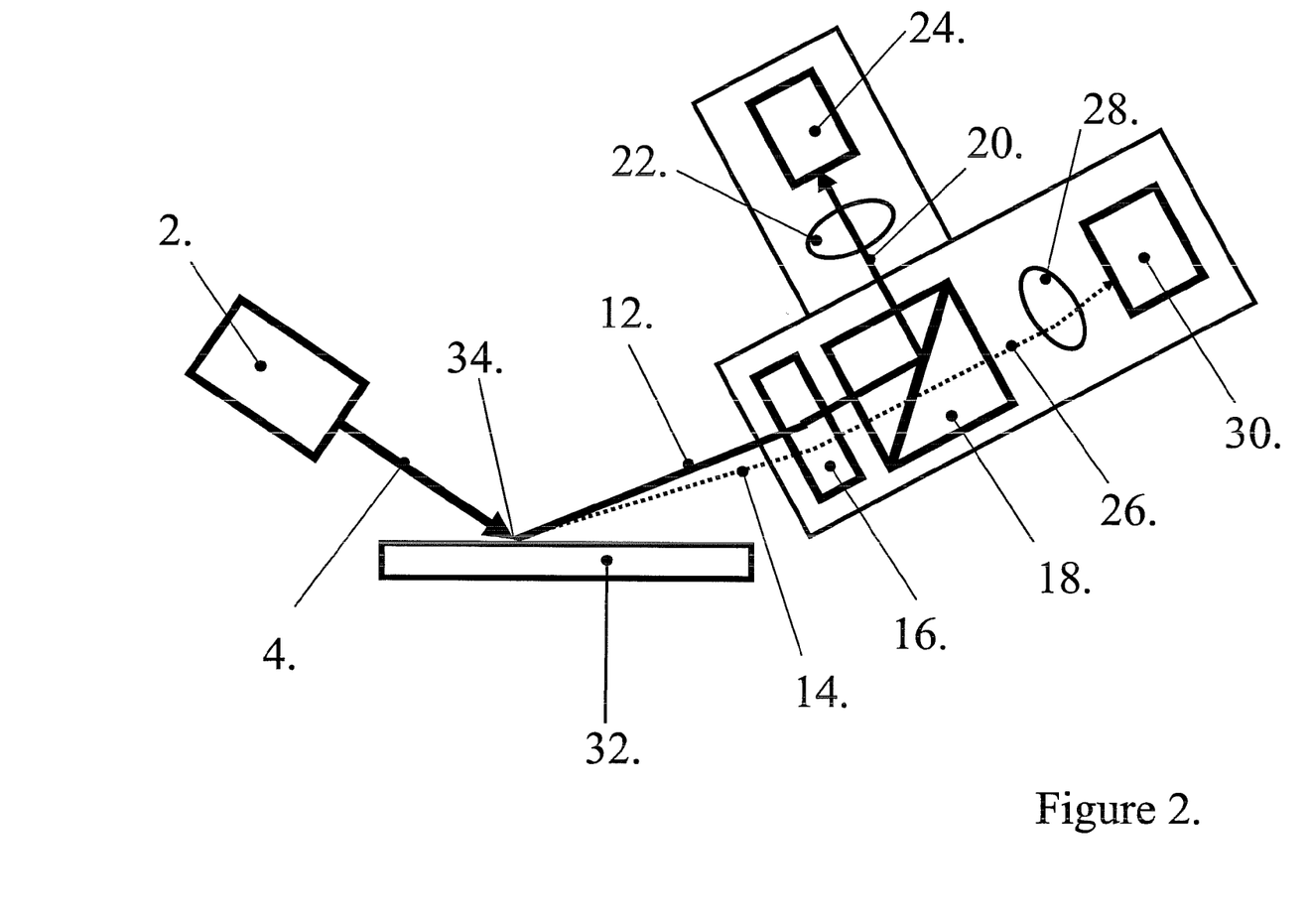
FIG. 2 is a schematic diagram which illustrates the application of PDS to characterise the polarmetric signature from the surface of a test object.

FIG. 2 illustrates how the basic components of the turbidity sensor illustrated in FIG. 1 can be adapted to characterise the polarmetric signature and scattering characteristics of an object surface. In this case, a laser 2 emitting a horizontally polarized stimulus beam 4 is directed onto a surface 34 of a test substrate 32. When the stimulus beam strikes surface 34, a portion of the reflected stimulus is scattered and becomes depolarized 14, while the majority of the reflected beam maintains its original horizontal linear polarization characteristics 12. These two reflected components (12 and 14) then pass through collimating system 16, polarization segregating unit 18, and focusing units (22 and 28) before falling upon their respective sensor units (24 and 30). It can be seen that in the absence of a highly scattering interface, the majority of the stimulus throughput is still linearly polarized 20, with minimal randomly polarized or scattered throughput 26.

Figure 3:
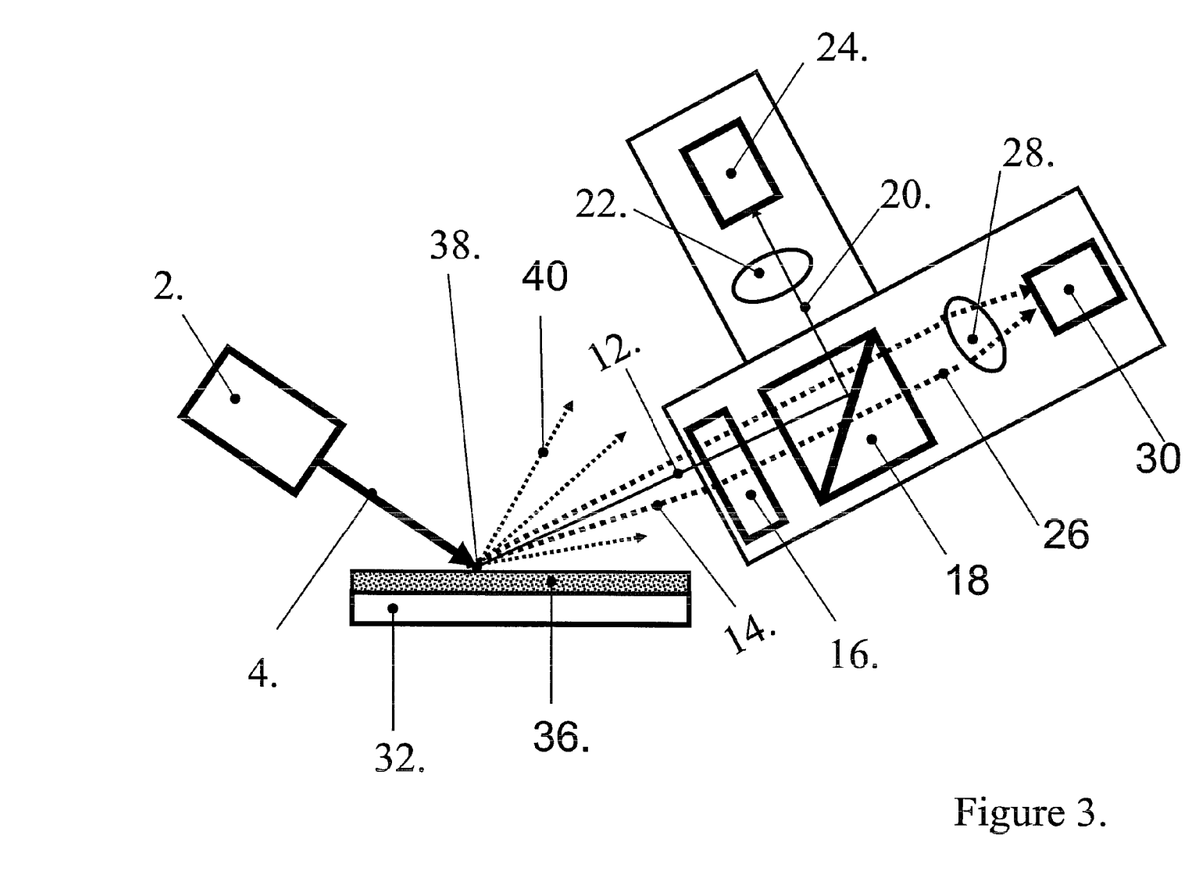
FIG. 3 is a schematic diagram that illustrates how a polarmetric signature of the surface of a test object can be altered by the presence of a scattering (or diachroic) media formed on or covering its surface. In this application, PDS can be utilised to detect the presence and quantify the amount of scattering media, (such as the build-up of ice on roads or aircraft structures, surface corrosion and pitting, or the presence of coatings with specific scattering or diachroic properties on underlying structural substrates).

FIG. 3 illustrates the change apparent in the stimulus throughput when the horizontally polarized stimulus 4 from laser 2 interacts with substrate 32 possessing a scattering interface 36. The linearly polarized stimulus undergoes significant scattering 38 and randomisation of its plane of polarization through interactions with scattering interface 36. As a result a larger proportion of the initially horizontally polarized stimulus becomes scattered and depolarized 40. Of the stimulus throughput entering the collimating system 16 there is a higher proportion of randomly polarized throughput 14 compared to the original stimulus polarization plane 12. Subsequently, the proportion of the stimulus throughput maintaining its original horizontal polarization orientation 20 as it passes through polarization segregation unit 18 is dramatically reduced compared to the random polarization components 26. A computational comparison of the outputs of sensors 24 and 30 will clearly indicate the presence of scattering interface 36 on underlying substrate 32.

Figure 4:
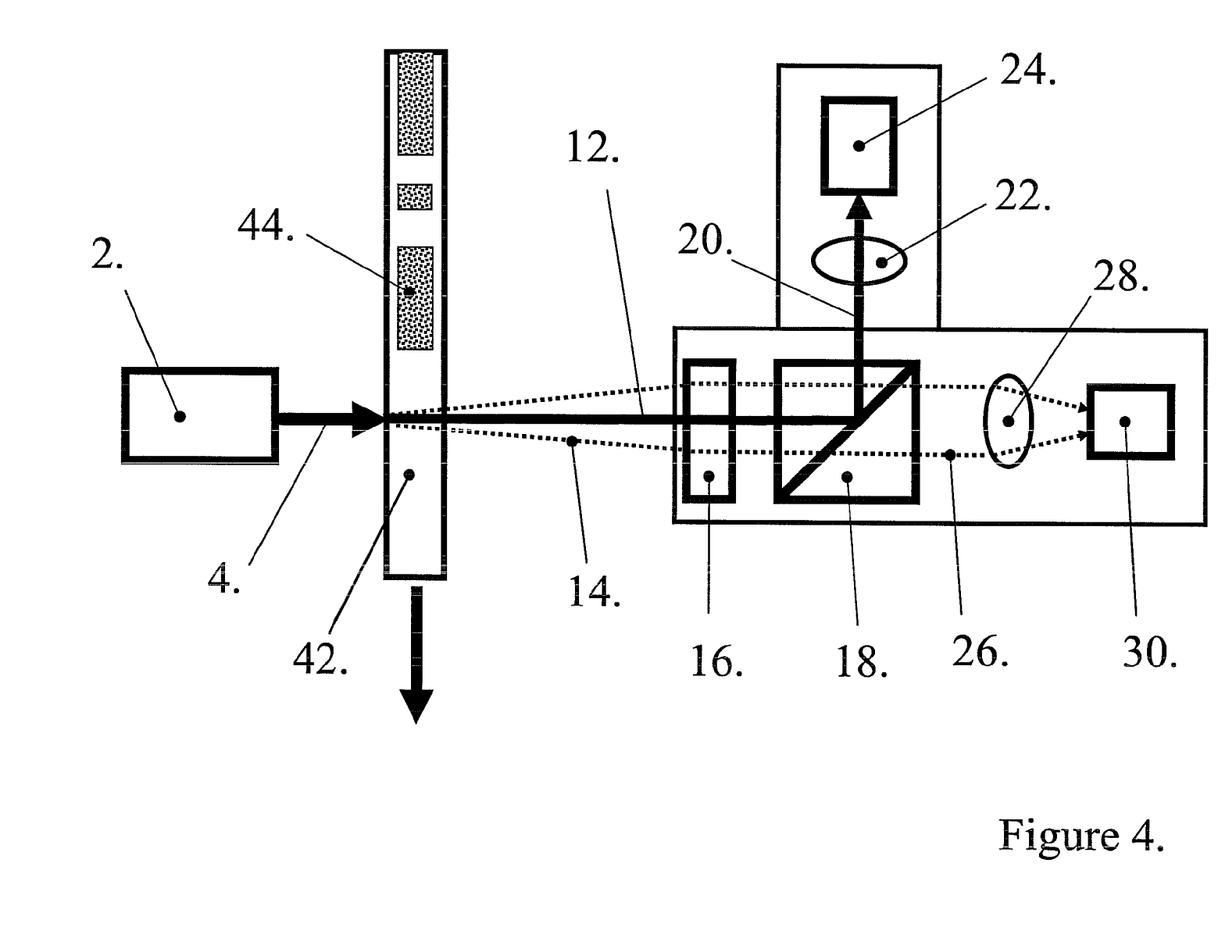
FIG. 4 is a schematic diagram that illustrates the application of PDS to the detection of spatial distributions of embedded scattering media within a transmissive substrate. In this figure the transmitted linearly polarized stimulus passes through the target object without interacting with the spatially restricted patterns of embedded scattering media.

FIG. 4 illustrates how the above components can be applied to detect the presence and spatial distribution of scattering media 44 imbedded in a electromagnetically transmissive material or structure 42. A linearly polarized stimulus source 2 emits a linearly polarized stimulus 4 at a wavelength that is capable of being transmitted through material or structure 42. Stimuli passing through the region of the sample which contain little or no embedded scattering medium undergoes very little scattering, and as a result the majority of the stimulus throughput maintains its original linear polarization state 12. As outlined above, the linear polarized 12 and depolarized 14 components passed through a collimating system 16 before being systematically redirected when passing through polarization segregation system 18. As previously described the proportion of the stimulus throughput maintaining its original horizontal polarization orientation 20 as it passes through polarization segregation unit 18 is compared to the random polarization components 26, through a computational comparison of the outputs of sensors 24 and 30.

Figure 5:
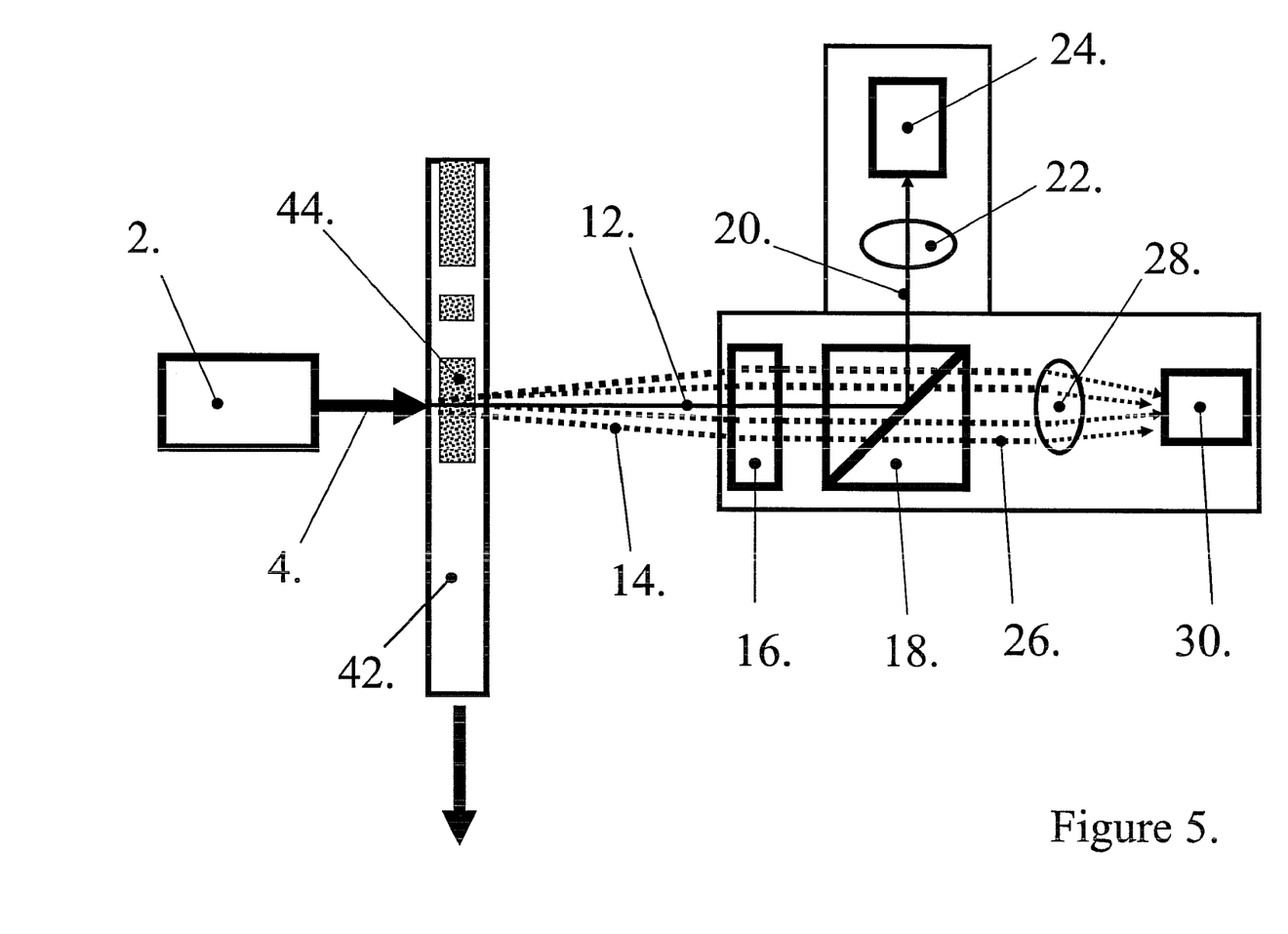
FIG. 5 is a schematic diagram that illustrates the resultant change in the PDI signature when the linearly polarized stimulus interacts with the spatial distribution of the embedded scattering media.

Referring to FIG. 5, this illustration demonstrates the scattering and depolarizing effects of embedded particles 44 within a material or structure 42. When the linearly polarized stimulus 4 interacts with embedded particles 44, the linearly polarized stimulus 4 undergoes significant depolarization and scattering. As a result, the proportion of depolarized 14 to linearly polarized 12 stimulus throughput dramatically increases. Such a system can be used in a variety of applications ranging from document security, nondestructive testing and diagnostic medical imaging (for example utilising linearly polarized x-rays for enhanced signal to noise ratio in comparison to typical x-rays or CT scans).

i. Operation:

Referring to FIG. 1, the present invention provides a real-time Method and System for the Polarmetric Analysis of Scattering Media. The system includes a linearly polarized illumination system 2 with a stimulus having a wavelength in the electromagnetic spectrum chosen to propagate through the intervening medium and match the turbidity sensing task (for example, at a wavelength which will be maximally scattered by the particles under study). The stimulus may be inherently polarized (as in the case of a laser), or maybe polarized through the application of polarizing filters or optics. The polarized stimulus 4, is of a wavelength and polarization orientation which is chosen to match the wavelength sensitivity and physical orientation of the polarization segregation system 18. In the absence of a scattering media, the linearly polarized stimulus will passed through the sample chamber 6, pass through collimating system 16, and will enter the polarization segregation system 18. The polarization segregation system is aligned in such a way as to effectively match the orientation of, and isolate the incoming linearly polarized stimulus 12. As the polarized stimulus passes through the sample media 8, it interacts with scattering particles 10. The stimulus exiting the chamber therefore now consists of both straight-through polarized 12 and scattered depolarized 14 components. Positioned after the sample chamber are the stimulus collimating system 16, the polarization segregation system 18, and focusing apparatus 22 and 28 that focus the transmitted stimuli onto two or more detectors 24 and 30. The sensor's respective polarization specific outputs are processed to create a "real-time" Polarization Different Sensing (PDS) signal to be used to compute a measurement of turbidity. In the present example, the polarized component of the stimulus throughput 12 interacts with a polarization beam splitting cube 18 in such a way that the polarized component of the stimulus throughput 20 is reflected onto detector 24. In contrast, the scattered and depolarized components of the stimulus throughput 26 passes through polarization beam splitter 18 and is focused onto a separate detector 30. The sensor's respective outputs are therefore polarization specific and are further process to create a "real-time" Polarization Different Sensing (PDS) signal to be used to compute a measurement of turbidity, absorption or scattering. In the absence of a scattering media, the linearly polarized stimulus will pass through the sample chamber, pass through the collimating system and will enter the polarization segregation system. The polarization segregation system is aligned in such a way to effectively match and isolate the incoming linearly polarized stimulus. In the case of laser illumination, linear polarization efficiency in the range of 500:1 is common. Of the 0.2% unpolarized component within the stimulus, very little will be randomly aligned at the radial orientation required to be isolated in the second channel of the polarization segregation system. As a result, the majority of the stimulus throughput will be translated into a signal in the first polarization segregation channel. In the presence of a scattering sample, the linearly polarized light entering the sample chamber will be scattered and depolarized proportional to the concentration of scattering particles. The result is a decrease in the proportion of linearly polarized throughput at the original orientation of the stimulus, and an increase in the proportion of throughput sampled at any other plane of linear polarization.

Such a process operates by calculating the percentage decrease in the direct transmission of a linearly polarized stimulus through (or reflected back from) a scattering medium. The most basic embodiment of this technique consists of inline emitter and detector units with the emitter producing a linearly polarized stimulus. The receiving detector a unit is comprised of a pair of detector subunits which are arranged so that each detector subunit is aligned to, and selective for the detection of specific orthogonal planes of linear polarization within a common stimulus input (there by being capable of Polarization Different Sensing). The emitter and detectors are separated by a space in which the transmissive sample is positioned or flows. As the number of suspended particles in a sample (or local density of particles along the stimulus pathway) increase, the sample becomes more opaque or turbid, resulting in a greater scattering and absorption of the polarized stimulus per given unit of distance transmitted through the Sample.

Variations:

The underlying principles of this Method and System for the Polarmetric Analysis of Scattering Medium is not limited to visible wavelengths within the electromagnetic spectrum. Indeed, infrared (IR), x-ray and microwave based systems would function, requiring only the appropriate stimulus sensors, emitters, and optical or waveguide components for the range of operating wavelengths. As such, the examples given are meant for illustrative purposes of the general underlying princles, and do not define the scope of the claims. The medium in which the particles are detected can be a liquid, a gas, a solid or a vacuum.

In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

It will be apparent to one skilled in the art that modifications may be made to the illustrated embodiment without departing from the spirit and scope of the invention as hereinafter defined in the Claims.

I claim:

1. A method for polarmetric analysis of scattering media, comprising:

directing stimulus from a linearly polarized stimulus source at a sample;

directing the stimulus coming from the sample through a collimating system onto a polarizing beam splitter reflecting light having the same linear polarization as the original linearly polarized stimulus source which causes the stimulus to be segregated into a linearly polarized unscattered component and a depolarized scattered component, light having the same linear polarization as the originally linearly polarized stimulus source is reflected to a first detector and light having differing polarizations pass through the polarizing beam splitter to a second detector; and computationally comparing the unscattered component and the scattered component to compute a measurement of one of turbidity, absorption or scattering.

2. An apparatus for polarmetric analysis of scattering media, comprising:

a linearly polarized source of stimulus for directing stimulus at a sample;

a collimating system for collimating the stimulus coming from the sample;

a polarizing beam splitter reflecting light having the same linear polarization as the original linearly polarized stimulus source for segregating the collimated stimulus into a linearly polarized unscattered component and a scattered depolarized component, light having the same linear polarization as the originally linearly polarized stimulus source is reflected to a detector and light having differing polarizations pass through the polarizing beam splitter; and means for computationally comparing the unscattered component and the scattered depolarized component to compute a measurement of one of turbidity, absorption or scattering.

* * * * *